(12) United States Patent
Burnett

(10) Patent No.: US 8,394,048 B2
(45) Date of Patent: *Mar. 12, 2013

(54) VESICULAR SHUNT FOR THE DRAINAGE OF EXCESS FLUID

(75) Inventor: Daniel Rogers Burnett, San Francsico, CA (US)

(73) Assignee: Sequana Medical AG, Zug (CH)

( * ) Notice: Subject to any disclaimer, the term of this patent is extended or adjusted under 35 U.S.C. 154(b) by 405 days.

This patent is subject to a terminal disclaimer.

(21) Appl. No.: 12/014,696

(22) Filed: Jan. 15, 2008

(65) Prior Publication Data

US 2008/0154173 A1    Jun. 26, 2008

Related U.S. Application Data

(62) Division of application No. 10/369,550, filed on Feb. 21, 2003, now Pat. No. 7,335,179.

(60) Provisional application No. 60/359,287, filed on Feb. 25, 2002, provisional application No. 60/389,346, filed on Jun. 18, 2002.

(51) Int. Cl.
*A61M 5/00* (2006.01)
*A61M 1/00* (2006.01)
*A61F 2/00* (2006.01)
*A61F 2/02* (2006.01)
*A61F 2/04* (2006.01)
*A61F 2/82* (2006.01)

(52) U.S. Cl. ............. 604/9; 604/8; 604/10; 623/1.15; 623/1.24; 623/23.64; 623/23.76

(58) Field of Classification Search ............. 604/9, 10, 604/541, 8; 606/107, 108, 151, 153; 623/1.11, 623/1.15, 1.24, 1.31, 1.42, 1.45, 1.46, 23.64, 623/23.76, 26
See application file for complete search history.

(56) References Cited

U.S. PATENT DOCUMENTS

| | | | |
|---|---|---|---|
| 3,516,410 A | | 6/1970 | Hakim |
| 3,540,451 A | * | 11/1970 | Zeman ............................ 604/27 |
| 3,575,158 A | | 4/1971 | Summers |
| 3,608,088 A | | 9/1971 | Dorman et al. |
| 3,626,950 A | | 12/1971 | Schulte |
| 3,642,004 A | * | 2/1972 | Osthagen et al. ............. 604/249 |
| 3,654,932 A | | 4/1972 | Newkirk et al. |
| 3,810,259 A | | 5/1974 | Summers |
| 3,910,283 A | | 10/1975 | Leveen |
| 4,083,786 A | | 4/1978 | Tsuda et al. |

(Continued)

FOREIGN PATENT DOCUMENTS

| | | |
|---|---|---|
| GB | 2 350 794 | 12/2000 |
| WO | WO 97/41799 | 11/1997 |

(Continued)

OTHER PUBLICATIONS

Rozenblit, Grigory N., Peritoneal-Urinary Drainage for Treatment of Refractory Ascites: A Pilot Study, Journal of Vascular & Interventional Radiology, Nov./Dec. 1998, 9(6):998-1005, NY.

(Continued)

*Primary Examiner* — Tatyana Zalukaeva
*Assistant Examiner* — Adam Marcetich
(74) *Attorney, Agent, or Firm* — Foley & Lardner LLP; Nicola A. Pisano; Christopher C. Bolten

(57) ABSTRACT

A transvesicular drainage device configured to drain excess fluid from a variety of locations in the human body into the bladder. The device may be used to treat ascites or any fluid collection within the body of a human or of a non-human mammal.

13 Claims, 8 Drawing Sheets

U.S. PATENT DOCUMENTS

| | | | |
|---|---|---|---|
| 4,261,341 A | | 4/1981 | Hakim et al. |
| 4,368,737 A | * | 1/1983 | Ash .................................. 604/175 |
| 4,416,657 A | * | 11/1983 | Berglund ............................ 604/9 |
| 4,418,693 A | * | 12/1983 | LeVeen et al. ................. 606/190 |
| 4,557,724 A | * | 12/1985 | Gregonis et al. ............... 604/502 |
| 4,584,994 A | | 4/1986 | Bamberger et al. |
| 4,595,390 A | | 6/1986 | Hakim et al. |
| 4,610,625 A | | 9/1986 | Bunn |
| 4,610,658 A | | 9/1986 | Buchwald et al. |
| 4,615,691 A | | 10/1986 | Hakim et al. |
| 4,618,343 A | | 10/1986 | Polaschegg |
| 4,657,530 A | * | 4/1987 | Buchwald et al. ................. 604/9 |
| 4,725,207 A | | 2/1988 | Buchwald et al. |
| 4,779,614 A | | 10/1988 | Moise |
| 4,850,955 A | | 7/1989 | Newkirk |
| 4,904,236 A | | 2/1990 | Redmond et al. |
| 4,950,232 A | | 8/1990 | Ruzicka et al. |
| 4,963,129 A | | 10/1990 | Rusch |
| 4,991,594 A | * | 2/1991 | Angelchik ..................... 128/898 |
| 5,021,048 A | | 6/1991 | Buckholtz |
| 5,037,385 A | * | 8/1991 | O'Byrne .......................... 604/28 |
| 5,071,408 A | | 12/1991 | Ahmed et al. |
| 5,078,688 A | | 1/1992 | Lobodzinski et al. |
| 5,147,281 A | | 9/1992 | Thornton et al. |
| 5,167,615 A | | 12/1992 | East et al. |
| 5,254,084 A | * | 10/1993 | Geary .............................. 604/29 |
| 5,356,386 A | | 10/1994 | Goldberg et al. |
| 5,360,414 A | | 11/1994 | Yarger |
| 5,385,541 A | | 1/1995 | Kirsch et al. |
| 5,387,188 A | | 2/1995 | Watson et al. |
| 5,395,350 A | | 3/1995 | Summers |
| 5,397,354 A | * | 3/1995 | Wilk et al. ....................... 604/28 |
| 5,431,637 A | | 7/1995 | Okada et al. |
| 5,472,323 A | | 12/1995 | Hirabayashi et al. |
| 5,474,683 A | | 12/1995 | Bryant et al. |
| 5,489,276 A | | 2/1996 | Jamshidi |
| 5,520,632 A | * | 5/1996 | Leveen et al. .................... 604/9 |
| 5,575,770 A | | 11/1996 | Melsky et al. |
| 5,637,083 A | | 6/1997 | Bertrand et al. |
| 5,725,506 A | | 3/1998 | Freeman et al. |
| 5,830,172 A | | 11/1998 | Leveen et al. |
| 5,902,336 A | * | 5/1999 | Mishkin ..................... 623/11.11 |
| 5,947,911 A | | 9/1999 | Wong et al. |
| 5,980,478 A | | 11/1999 | Gorsuch et al. |
| 5,980,480 A | * | 11/1999 | Rubenstein et al. ............... 604/9 |
| 5,989,207 A | * | 11/1999 | Hughes ............................. 604/8 |
| 6,007,511 A | | 12/1999 | Prywes |
| 6,017,355 A | * | 1/2000 | Hessel et al. .................. 606/184 |
| D420,738 S | | 2/2000 | Carter et al. |
| 6,022,333 A | | 2/2000 | Kensey |
| 6,027,442 A | * | 2/2000 | Von Iderstein .................. 600/29 |
| 6,132,415 A | | 10/2000 | Finch et al. |
| 6,162,238 A | | 12/2000 | Kaplan et al. |
| 6,162,487 A | * | 12/2000 | Darouiche ................... 427/2.14 |
| 6,193,684 B1 | | 2/2001 | Burbank et al. |
| 6,254,567 B1 | | 7/2001 | Treu et al. |
| 6,264,625 B1 | | 7/2001 | Rubenstein et al. |
| 6,417,750 B1 | | 7/2002 | Sohn |
| 6,436,087 B1 | | 8/2002 | Lewis et al. |
| 6,533,733 B1 | * | 3/2003 | Hylton et al. ................. 600/561 |
| 6,648,906 B2 | * | 11/2003 | Lasheras et al. .............. 607/105 |
| 6,689,085 B1 | | 2/2004 | Rubenstein et al. |
| 6,827,682 B2 | | 12/2004 | Bugge et al. |
| 6,846,168 B2 | | 1/2005 | Davis |
| 6,875,192 B1 | | 4/2005 | Saul et al. |
| 6,887,214 B1 | | 5/2005 | Levin et al. |
| 6,894,456 B2 | | 5/2005 | Tsukamoto et al. |
| 6,905,474 B2 | | 6/2005 | Borgensen |
| 6,926,691 B2 | | 8/2005 | Miethke |
| 6,955,655 B2 | | 10/2005 | Burbank et al. |
| 7,025,739 B2 | | 4/2006 | Saul |
| 7,025,742 B2 | | 4/2006 | Rubenstein et al. |
| 7,128,735 B2 | | 10/2006 | Weston |
| 7,195,608 B2 | | 3/2007 | Burnett |
| 7,311,690 B2 | | 12/2007 | Burnett |
| 7,335,179 B2 | | 2/2008 | Burnett |
| 7,419,483 B2 | | 9/2008 | Shehada |
| 2001/0025170 A1 | | 9/2001 | Paderni |
| 2002/0013545 A1 | | 1/2002 | Soltanpour et al. |
| 2002/0022793 A1 | | 2/2002 | Bertrand et al. |
| 2002/0107467 A1 | * | 8/2002 | Levin ........................... 604/4.01 |
| 2004/0049288 A1 | | 3/2004 | Levin |
| 2005/0096582 A1 | | 5/2005 | Burnett |
| 2005/0131340 A1 | | 6/2005 | Sorenson et al. |
| 2005/0273034 A1 | | 12/2005 | Burnett |
| 2006/0036208 A1 | | 2/2006 | Burnett |
| 2006/0058731 A1 | | 3/2006 | Burnett et al. |
| 2007/0106205 A1 | | 5/2007 | Connell et al. |
| 2008/0108935 A1 | | 5/2008 | Nyhart, Jr. |

FOREIGN PATENT DOCUMENTS

| | | |
|---|---|---|
| WO | WO 98/16171 | 4/1998 |

OTHER PUBLICATIONS

U.S. Appl. No. 11/933,214, filed Oct. 31, 2007, Burnett.

Costanzo et al., "Early Ultrafiltration in Patients with Decompensated Heart Failure and Diuretic Resistance," J. Am. Coll. Cardiol., vol. 46 (11), pp. 2047-2051 (2005).

Fioulberg et al., "Terminal Right Heart Failure Due to Complex Congenital Cardiac Disease Successfully Managed by Ilome Peritoneal Drainage," Cardiol. Young, vol. 13, pp. 568-570 (2003).

Ortiz et al., "Long-Term Automated Peritoneal Dialysis in Patients with Refractory Congestive Heart Failure," Advances in Peritoneal Dialysis, vol. 19, pp. 77-80 (2003).

International Search Report for PCT/US03/05145, 3 pages (mailed Jul. 17, 2003).

USPTO, Supplemental Notice of Allowability for U.S. Appl. No. 10/369,550, 2 pages (mailed Dec. 17, 2007).

USPTO, Notice of Allowance and Fees Due for U.S. Appl. No. 10/369,550, 4 pages (mailed Sep. 24, 2007).

USPTO, Non-Final Office Action for U.S. Appl. No. 10/369,550, 13 pages (mailed Mar. 09, 2006).

USPTO, Corrected Notice of Allowance and Fees Due for U.S. Appl. No. 10/700,863, 5 pages (mailed Nov. 08, 2007).

USPTO, Notice of Allowance and Fees Due for U.S. Appl. No. 10/700.863, 7 pages (mailed Nov. 2, 2006).

USPTO, Non-Final Office Action for U.S. Appl. No. 10/700,863, 11 pages (mailed Feb. 2, 2006).

USPTO, Supplemental Notice of Allowability for U.S. Appl. No. 11/198,079, 2 pages (mailed Jan. 9, 2007).

USPTO, Notice of Allowance and Fees Due for U.S. Appl. No. 11/198,079, 4 pages (mailed Oct. 5, 2006).

USPTO, Non-Final Office Action for U.S. Appl. No. 11/198,079, 7 pages (mailed Feb. 2, 2006).

USPTO, Non-Final Office Action for U.S. Appl. No. 11/181,539, 10 pages (mailed Sep. 16, 2008).

USPTO, Final Office Action for U.S. Appl. No. 11/181,539, 10 pages. (mailed Mar. 18, 2008).

USPTO, Non-Final Office Action for U.S. Appl. No. 11/181,539, 8 pages (mailed May 22, 2007).

USPTO, Final Office Action for U.S. Appl. No. 11/181,539, 6 pages (mailed Oct. 10, 2006).

USPTO, Non-Final Office Action for U.S. Appl. No. 11/181,539, 8 pages (mailed Jan. 7, 2006).

USPTO, Final Office Action for U.S. Appl. No. 10/826,237, 10 pages (mailed Oct. 28, 2008).

USPTO, Non-Final Office Action for U.S. Appl. No. 10/826,237, 10 pages (mailed Feb. 22, 2008).

USPTO, Final Office Action for U.S. Appl. No. 10/826,237, 10 pages (mailed Jul. 5, 2007).

USPTO, Non-Final Office Action for U.S. Appl. No. 10/826,237, 8 pages (mailed Dec. 19, 2006).

USPTO, Office Action mailed Dec. 19, 2006, U.S. Appl. No. 10/826,237.

USPTO, Final Office Action mailed Jul. 05, 2007, U.S. Appl. No. 10/826,237.

USPTO, Advisory Action mailed Nov. 20, 2007, U.S. Appl. No. 10/826,237.

USPTO, Office Action mailed Feb. 22, 2008, U.S. Appl. No. 10/826,237.

USPTO, Final Office Action mailed Oct. 28, 2008, U.S. Appl. No. 10/826,237.
USPTO, Office Action mailed Apr. 13, 2009, U.S. Appl. No. 10/826,237.
USPTO, Office Action mailed Jan. 27, 2006, U.S. App. No. 11/181,539.
USPTO, Final Office Action mailed Oct. 10, 2006, U.S. Appl. No. 11/181,539.
USPTO, Office Action mailed May 22, 2007, U.S. Appl. No. 11/181,539.
USPTO, Final Office Action mailed Mar. 18, 2007, U.S. Appl. No. 11/181,539.
USPTO, Office Action mailed Sep. 16, 2008, U.S. Appl. No. 11/181,539.
USPTO, Notice of Allowance with reasons for allowance mailed Jul. 20, 2009, U.S. Appl. No. 11/181,539.
USPTO, Final Office Action mailed Dec. 13, 2006, U.S. Appl. No. 10/369,550, 4 pages.
USPTO, Non-Final Office Action mailed Mar. 9, 2006, U.S. Appl. No. 10/369,550, 13 pages.
USPTO, Notice of Allowance with reasons for allowance mailed Jul. 20, 2009, U.S. Appl. No. 11/181,539, 9 pages.
USPTO, Advisory Action mailed Jul. 14, 2008, U.S. Appl. No. 11/181,539, 3 pages.
USPTO, Non-Final Office Action mailed Jan. 27, 2006, U.S. Appl. No. 11/181,539, 8 pages.
USPTO, Final Office Action mailed Jan. 05, 2010, U.S. Appl. No. 10/826,237, 13 pages.
USPTO, Advisory Action mailed Nov. 20, 2007, U.S. Appl. No. 10/826,237, 3 pages.
USPTO, Non-Final Office Action mailed Apr. 6, 2010, U.S. Appl. No. 11/933,214, 18 pages.

* cited by examiner

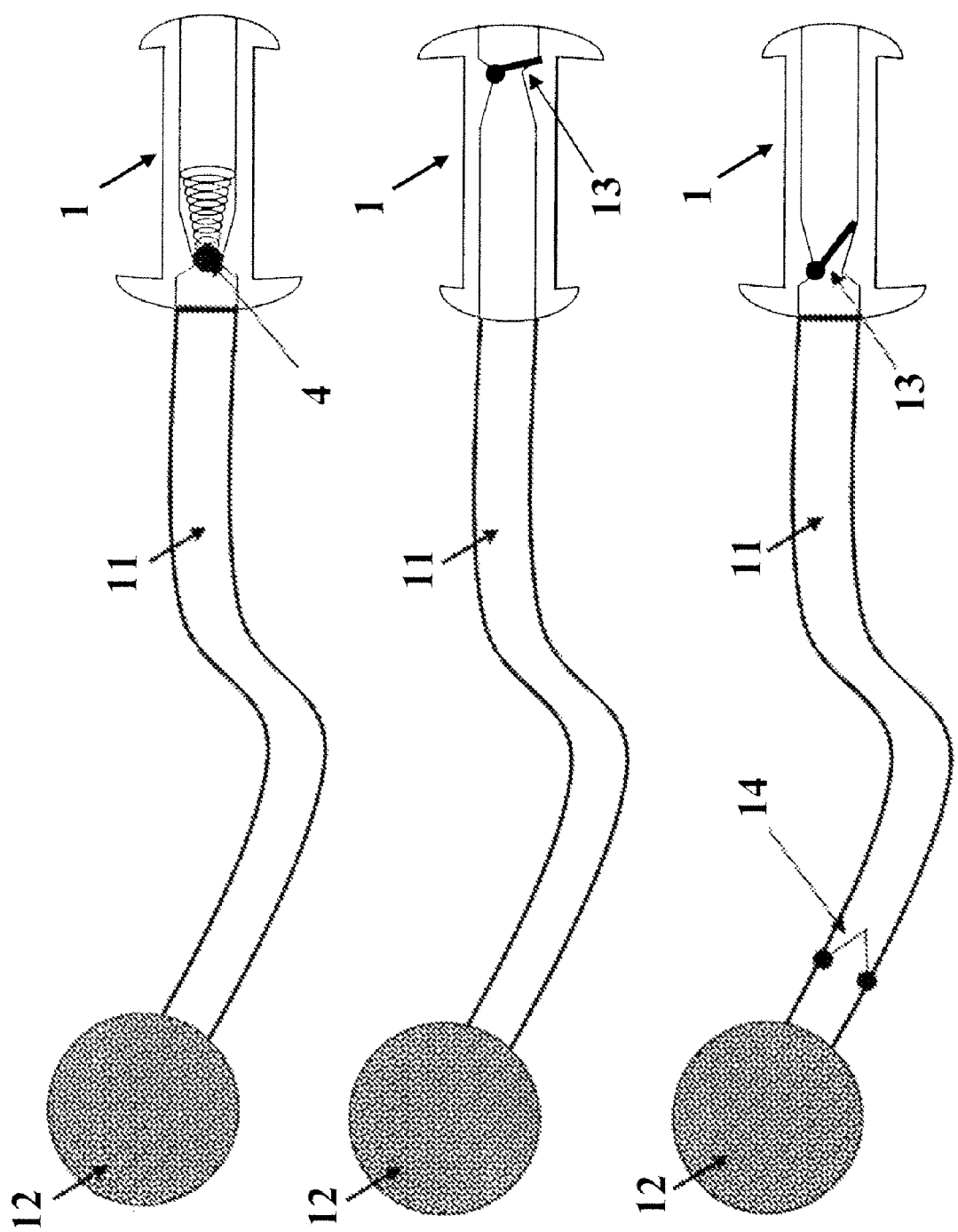

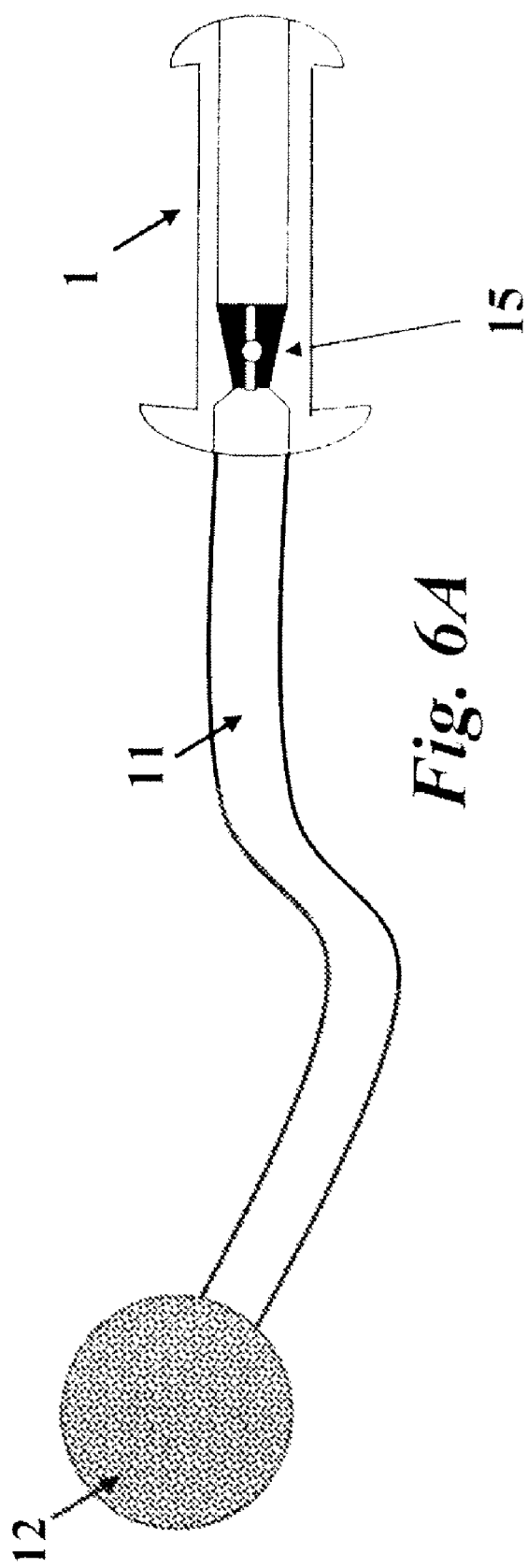
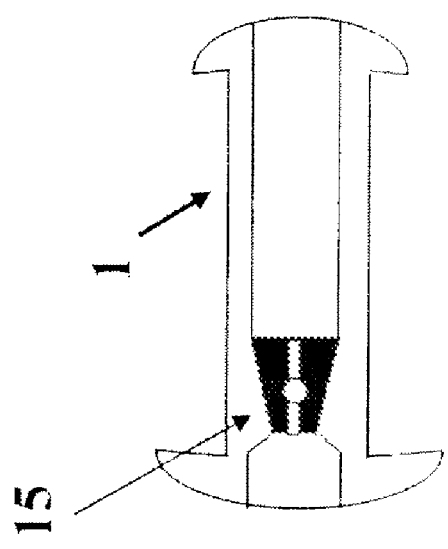
Fig. 6A
Fig. 6B

VESICULAR SHUNT FOR THE DRAINAGE OF EXCESS FLUID

CROSS-REFERENCE TO RELATED APPLICATIONS

This application is a divisional application of U.S. application Ser. No. 10/369,550 filed on Feb. 21, 2003, which claims the priority of U.S. Provisional Application Ser. No. 60/359,287 filed on Feb. 25, 2002 and U.S. Provisional Application Ser. No. 60/389,346 filed on Jun. 18, 2002, the entireties of which are incorporated herein by reference.

FIELD OF THE INVENTION

The present invention relates to a transvesicular drainage device designed to drain excessive fluid from a bodily cavity into the bladder. More particularly, the present invention relates to a vesicular drainage device that may be coupled to the bladder's wall and control flow of excess fluid from a region of the body into the bladder.

BACKGROUND OF THE INVENTION

In medicine there are a variety of conditions which result in pathologic chronic collection of bodily fluids. Chronic pericardial effusions, normopressure hydrocephalus, hydrocephalus, chronic pulmonary effusion, and ascites are but a few of the conditions in which chronic fluid collections persist and result in increased morbidity and mortality. These conditions currently are treated by different methods, more particularly: (1) external drainage with a high-risk of infection and long-term requirement for multiple punctures, (2) drainage to another body-cavity, or (3) various drugs.

For pericardial effusions and hydrocephalus of all types, the treatment of choice is drainage to another region of the body. This treatment entails a pericardial window, a highly invasive procedure in which a large section of the external heart cavity is removed. For hydrocephalus, the treatment of choice typically involves the use of a ventriculo-peritoneal shunt draining the cerebrospinal fluid into the peritoneal cavity. Unfortunately, this device frequently becomes clogged due to the proteinaceous environment of the peritoneal cavity and requires removal or revision.

More particularly, ascites is a highly debilitating complication associated with many medical conditions including liver failure and congestive heart failure. Untreated ascites can result in respiratory compromise, compression of the inferior vena cava (a vital blood vessel) and spontaneous bacterial peritonitis (a life-threatening condition). In order to treat chronic ascites, medicine has turned to both drugs and surgery.

The drugs required to treat ascites are typically long-term and frequently result in complications. The most common pharmaceutical treatment of ascites involves the use of diuretics to remove fluid from patient's body through their urine. The difficulty with this treatment is that fluid is removed from the entire body, including the circulating volume of blood, and can result in excessive loss of fluid required to perfuse the vital organs of the human body. Thus, even with religious application, drug treatments frequently fail and surgical, or invasive, procedures become necessary.

The current treatment of choice is called paracentesis. In paracentesis, the peritoneal fluid is drained through the abdominal wall via the insertion of a needle through the abdominal wall into the peritoneal cavity. Unfortunately, this procedure is only a temporary fix as the ascites quickly refills the peritoneal cavity in most chronic conditions. Furthermore, repeated paracenteses put the patient at increased risk for a life-threatening infection of their peritoneal cavity. Other surgical/invasive procedures involve treatment of the cause of the ascites (for example the Transjugular Intrahepatic Portosystemic Shunt) but these measures also frequently result in complications, which are often serious, and are thus performed hesitantly.

None of the existing devices are able to drain the peritoneal cavity except through temporary transabdominal insertion of a drainage catheter. These devices provide little improvement over the intermittent punctures of paracentesis and result in increased rates of infection if left in place for any length of time. The present invention will obviate the need for a long-term abdominal incision and, therefore, will eliminate the associated increased risk of serious infection.

SUMMARY OF THE INVENTION

The present invention relates to a device designed for implantation in the wall of the bladder that permits the drainage of excessive fluid into the bladder.

In one embodiment, this device includes a hollow, cylindrical column with flanges at both ends to provide secure anchorage in the bladder wall. Preferably there is a mechanism to provide unidirectional flow of fluid and prevent reflux of urine inside the column. A preferred embodiment of the device provides a passive ball-valve mechanism, which allows for drainage of fluid into the bladder whenever a certain pressure is achieved at the collection site. Another preferred embodiment of the device provides an active valve mechanism, which allows for controlled drainage of fluid into the bladder whenever the valve is actuated. The most preferred embodiment of the device includes a pump in addition to an active valve mechanism.

The present invention avoids the difficulties associated with the current therapies for chronic ascites, namely, the procedure allows the drainage of peritoneal fluid without (1) the serious complications of pharmaceuticals, (2) the inconvenience, the substantial costs and the increased risk of infection associated with frequent paracenteses, and (3) the multiple severe complications associated with more invasive and risky surgical operations to treat the cause of ascites.

When used to treat ascites, a device according to the present invention can be implanted either through a transurethral or transabdominal route. In order to drain other sites, the bladder component is implanted as above, and a flexible tube or other conduit may be incorporated to place the receptacle end of the device in a fashion tailored to the region to be drained. More specifically, such embodiment pertains to a peritoneo-vesicular drainage device permitting unidirectional flow of peritoneal fluid from the peritoneal cavity into the bladder.

In all embodiments, it is preferred that the device be constructed with biocompatible materials.

Methods of use of devices according to the present invention are also disclosed herein.

BRIEF DESCRIPTION OF THE DRAWINGS

FIG. 5 is an illustration of alternative embodiments of the invention with differing valve types, differing valve positioning and differing number of valves.

FIG. 6 is an illustration of an alternative embodiment of a device according to the present invention, in which an active, externally or internally controlled valve is utilized.

DETAILED DESCRIPTION OF EMBODIMENTS OF THE INVENTION

Figure 1:
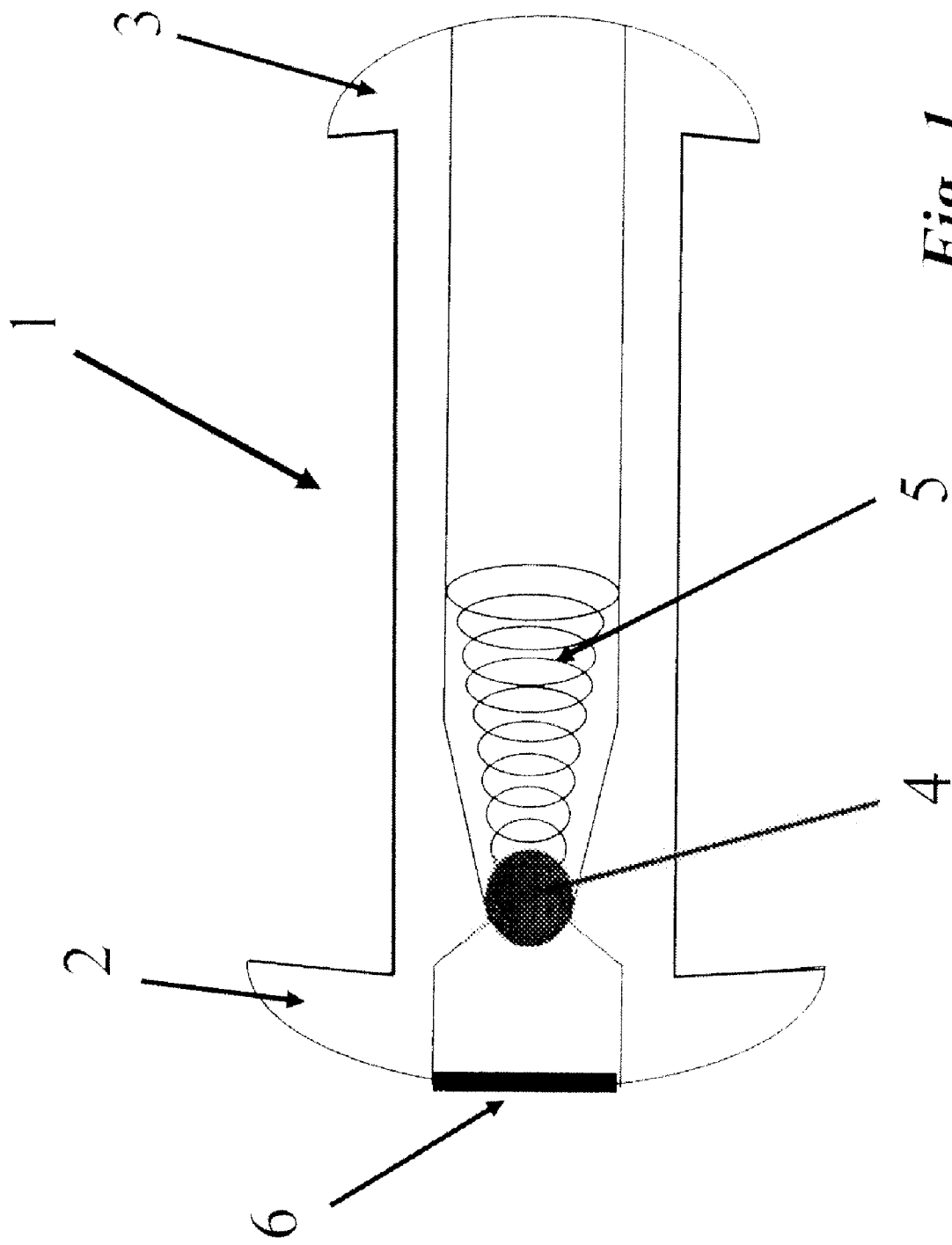
FIG. 1 shows a cross-sectional view of a device according to an embodiment of the present invention.

As can be seen in FIG. 1, a first embodiment of the present invention provides a novel vesicular drain 1 for implantation in the bladder wall 9, allowing unidirectional drainage of fluid into the bladder. The drain 1 includes two flanges at its ends 2, 3, which provide for the device to be firmly anchored once placed across the bladder wall 9. Alternative embodiments of the device may use other anchoring mechanisms, including, but not limited to: a screw thread on the outside of 1, staples, sutures, an adhesive compound, and/or one or more barbs.

The hollow shaft of the device contains a ball-valve 4 through which a positive closing pressure is provided by an attached spring 5.

The fluid collection interface of the device 1 may optionally include a large pore mesh 6 to allow for free flow of fluid while preventing incarceration of tissues at the drainage site.

Figure 2:
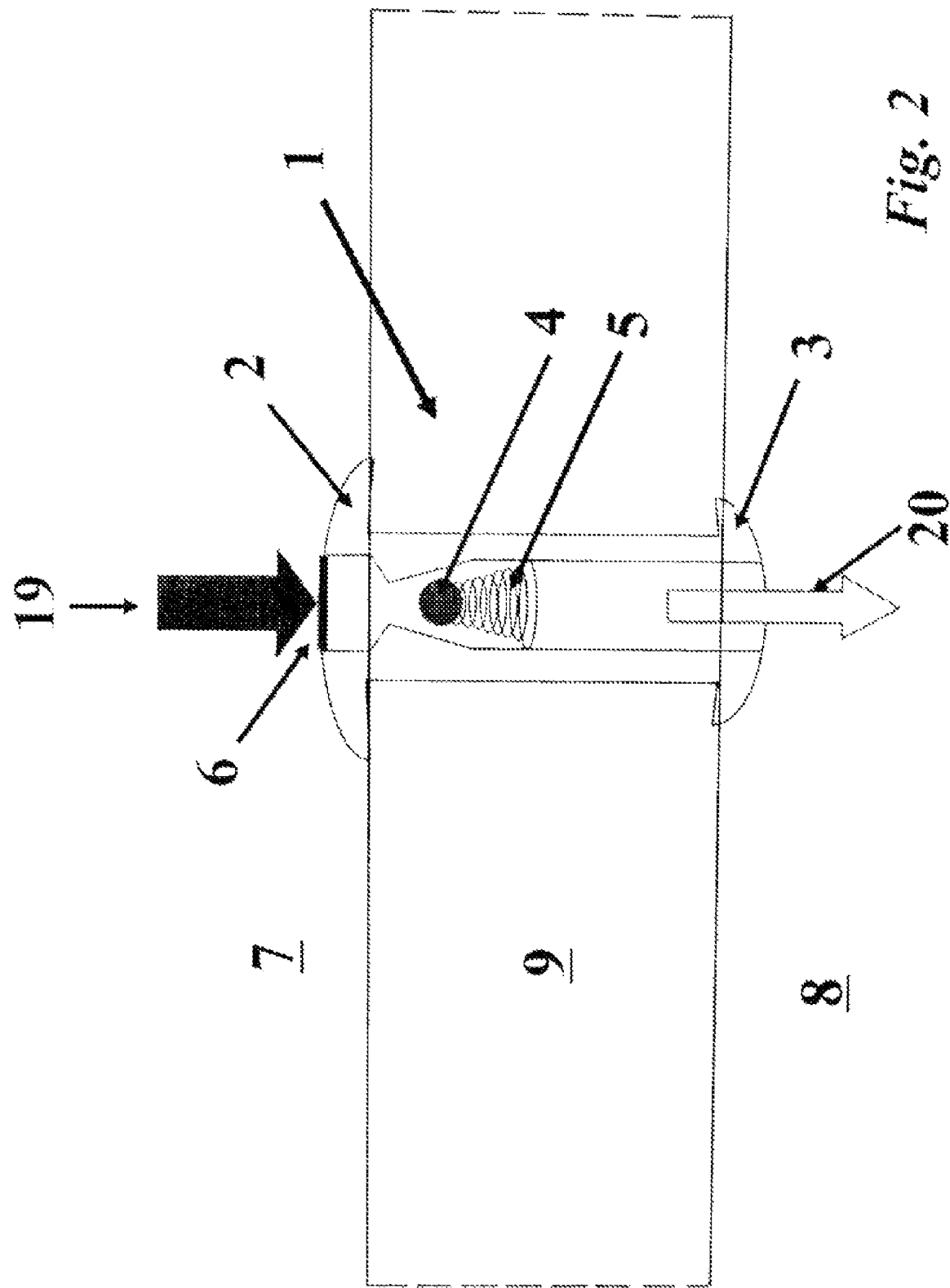
FIG. 2 shows a cross-sectional view of the device of FIG. 1 to treat ascites 1 after implantation, when the peritoneal pressure is sufficient to permit drainage.

As can be seen in FIG. 2, once the pressure of the fluid collection (in this case the peritoneal cavity) 7 exceeds the combined force of the spring 5 and the pressure of the fluid-filled bladder cavity 8, the peritoneal fluid 19 flows into the bladder cavity 8 through displacement of the ball-valve 4. There, the peritoneal fluid mixes with the urine 20.

Figure 3:
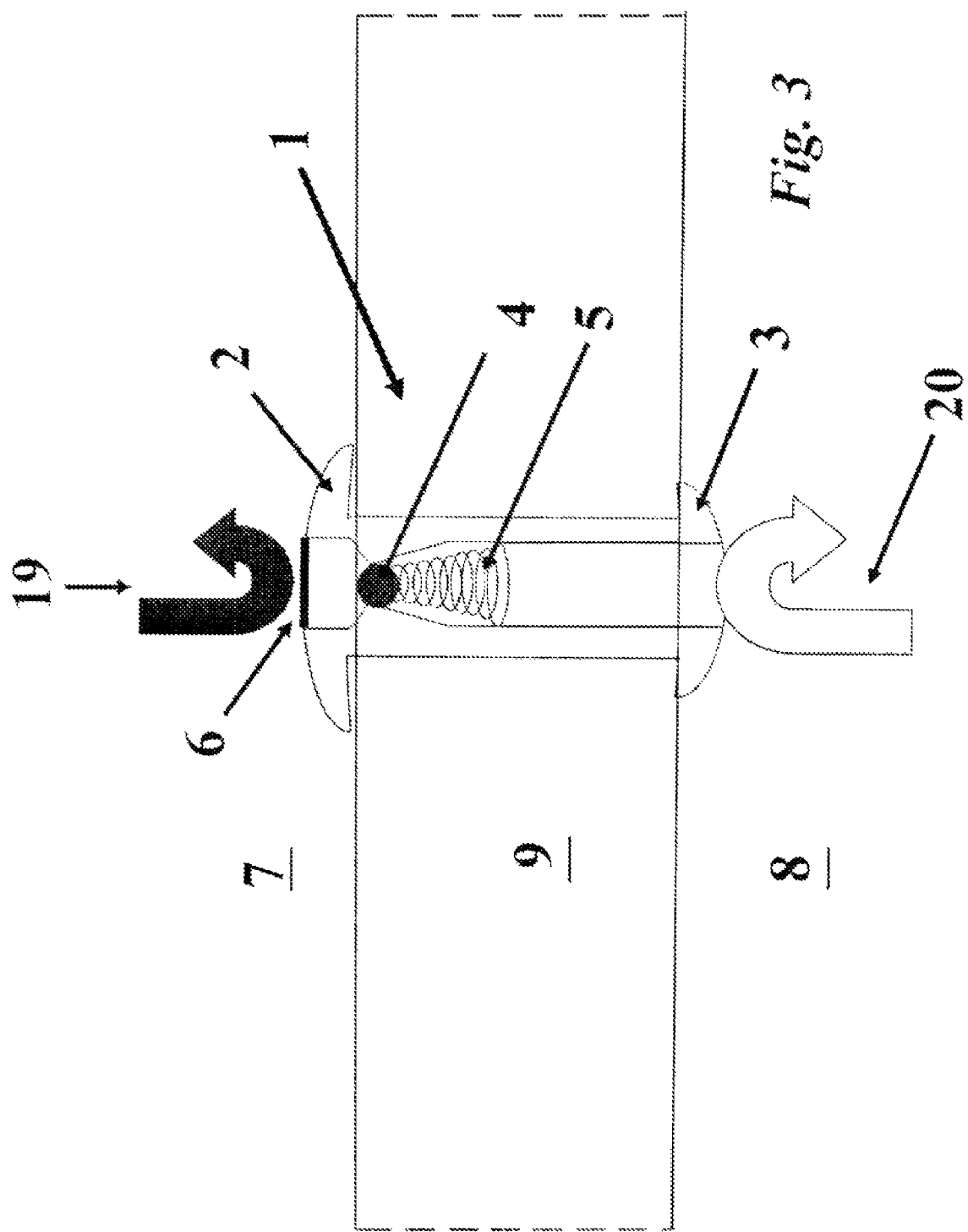
FIG. 3 shows a cross-sectional view of the device of FIG. 1 to treat ascites after implantation, when the peritoneal pressure is not sufficient to open the valve and no fluid flow occurs.

If the pressure of the bladder cavity 8 and the force of the spring 5, though, are greater than the pressure of the fluid collection (in this case the peritoneal cavity) 7, then the valve 4 will remain closed preventing reflux of urine 19 into the peritoneal cavity as depicted in FIG. 3.

Figure 4:
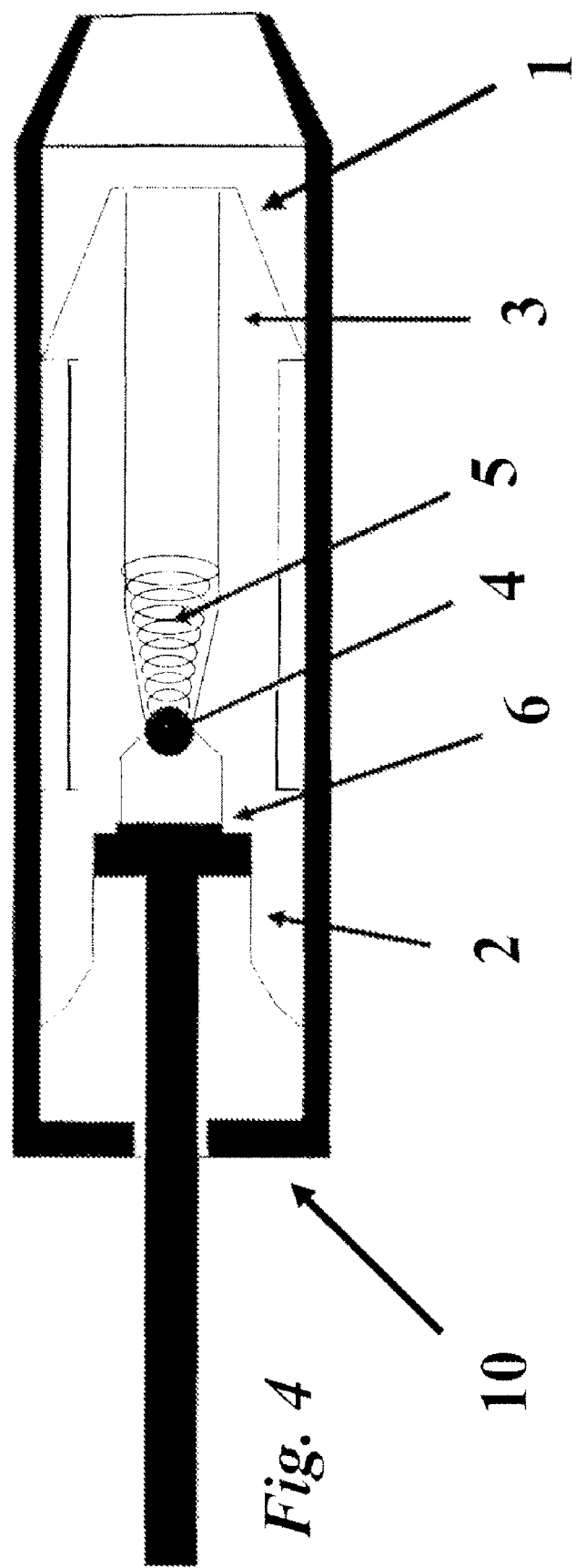
FIG. 4 is an illustration of an example of an insertion device through which a device according to the present invention can be implanted in the bladder wall.

The device is designed to be placed transurethrally or trans-abdominally via an insertion device 10 such as that depicted in FIG. 4. The method of insertion allows for a single invasive procedure to provide a long-term solution to the otherwise difficult problem of refractory, chronic ascites.

Alternatively, the device may contain a length of tubing 11 or other means of fluid transport to reach the fluid collection as well as an optional perforated receptacle 12, 17 and 18 through which the fluid collection will drain into the tubing. Such other means of fluid transport include, but are not limited to, conduit, catheter, channel, lumen, hose, pipe, duct, artery or vessel. The device may contain one or more valves of a variety of types including passive valves 4, 13 (flapper-valve), 14 (in FIG. 5), or active valves 15 (in FIG. 6) for tighter control of fluid drainage.

Figure 7:
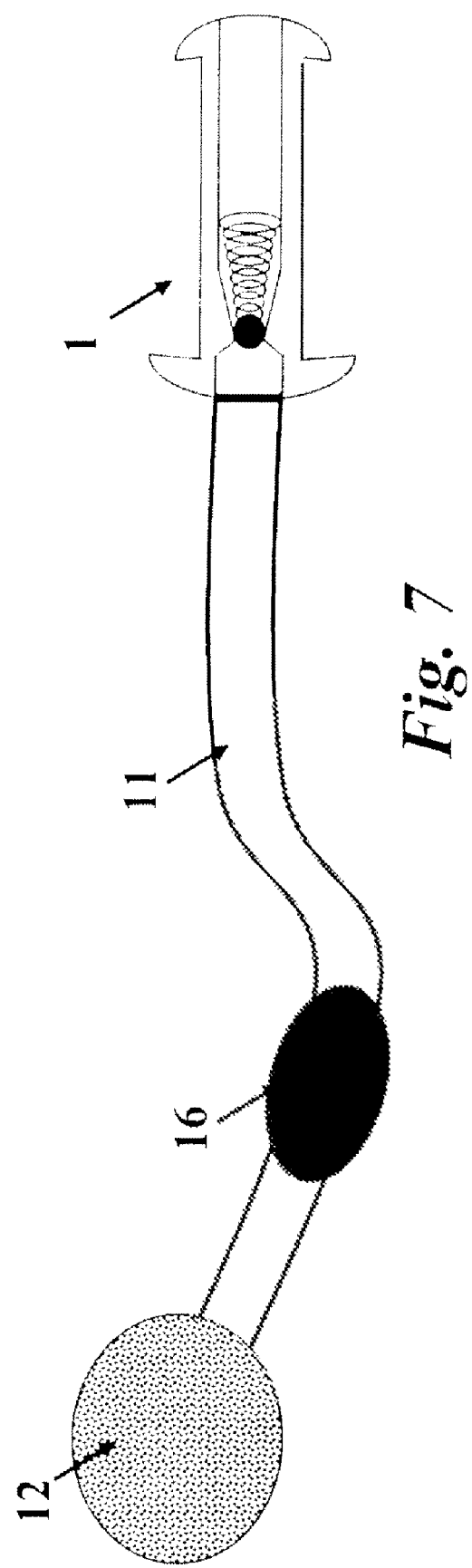
FIG. 7 is an illustration of an alternative embodiment of a device according to the present invention, in which a pump is included along the length of the tubing and placed subcutaneously for external control of drainage with a passive valve.

The device is also designed to be able to incorporate a pump mechanism 16 as shown in FIG. 7 which, when placed subcutaneously, can be actuated to provide an active pumping mechanism with the passive valves 4, 13, 14, or with an active valve 15. A third embodiment of the invention involves a unidirectional pump in place of the valve, controlling the flow of fluid through the device. A fourth embodiment of the invention involves a single unidirectional valve controlling the flow of fluid through the device.

Alternatively, maneuvers which increase the pressure of the fluid cavity can also be utilized with the passive valves 4, 13, 14 to affect drainage such as bearing down to increase intraabdominal pressure to drain the peritoneal cavity or application of a girdle designed to increase abdominal pressure.

Figure 8C:
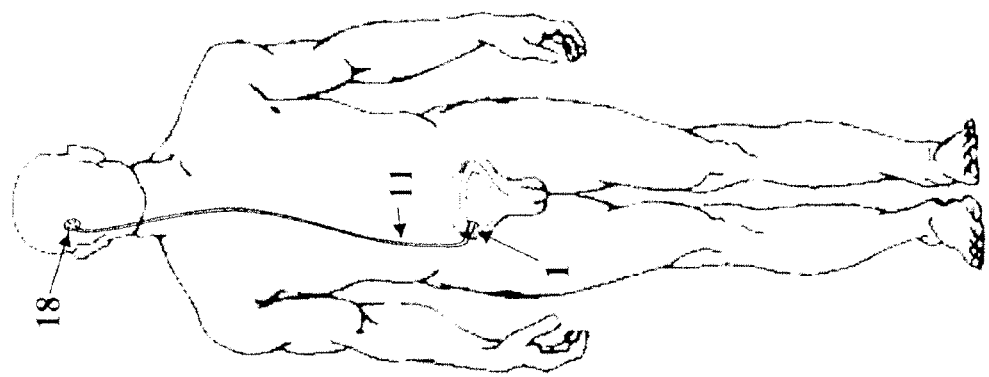
FIG. 8 is an illustration of a few of the alternative embodiment of a device according to the present invention, in which the peritoneal cavity, the pulmonary space and the ventricular space are able to be drained (pericardial drainage device not shown).
Figure 8B:
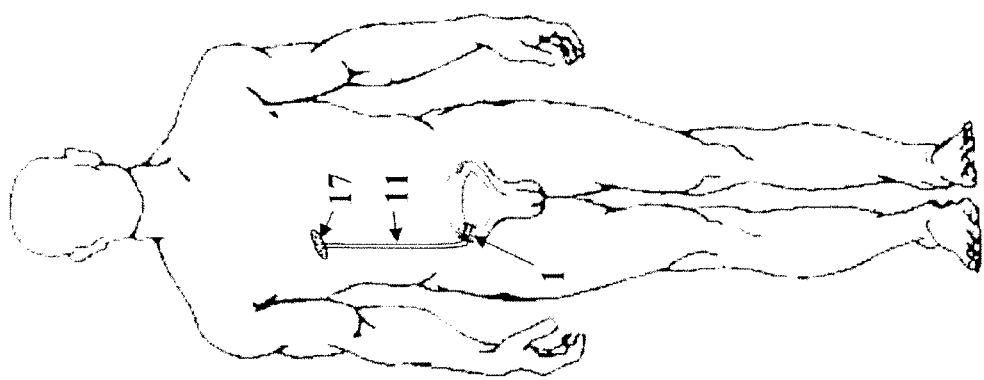
Figure 8A:
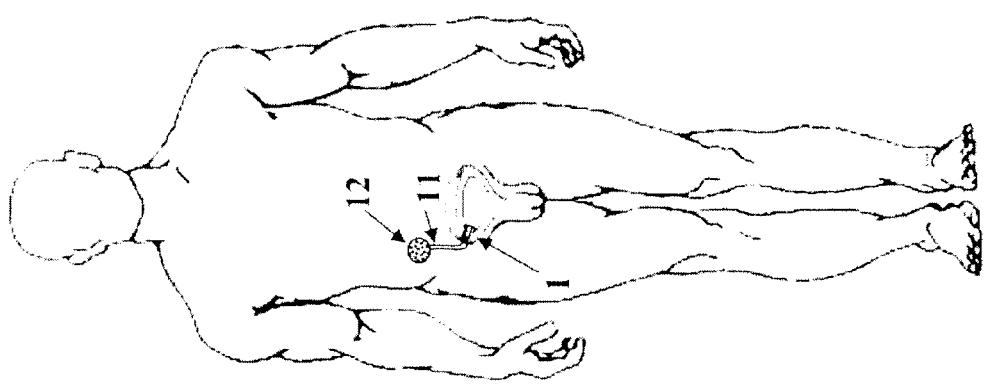

The device will be designed to drain a variety of different fluid collections including, but not limited to, the peritoneal cavity FIG. 8A, pulmonary effusions FIG. 8B and excessive cerebrospinal fluid FIG. 8C. Pericardial effusion drain is not shown.

Of particular interest to the inventors is the use of the invention to drain pulmonary effusions and other fluid collections in the lungs, in FIG. 8B.

While these are the preferred embodiments, the device could employ any mechanism which provides a unidirectional passive or active valve for the drainage of any body fluid into the urinary bladder. This could involve filtration of the fluid through a polymer so as to sequester albumin and other proteins in the fluid collection while allowing flow of water and ions across the semi-permeable membrane. This could also involve an electronic valve triggered via communication across the tissues of the human body through EMFs such as radio, electricity, pressure, mechanical, magnetism, or other means of communication, allowing drainage only at selected times.

The valve of the device can take many shapes and the device can be manufactured from any of a variety of materials with the only requirement being that of biocompatibility. Alternatively, the device, in either the active or passive embodiment, may incorporate anti-infective components in order to prevent the spread of infection between the body cavities. Such anti-infective components include, but are not limited to, bacteriostatic materials, bacteriocidal materials, one or more antibiotic dispensers, antibiotic eluting materials, entrained radioisotopes, a heating element, bioactive plastics, surfaces which encourage epithelialization, and coatings which prevent bacterial adhesion.

Alternatively, the device, in either the active or passive embodiment, may incorporate anti-clogging components. Such anti-clogging components include, but are not limited to, an active ultrasonic component, an inner and outer sleeve which, when actively agitated, disrupt the inner lumen, surfaces which encourage epithelialization, enzyme eluting materials, enzyme eluting materials which specifically target the proteinaceous components of ascites, chemical eluting surfaces, an intermittent plunger mechanism, and coatings which prevent adhesion of proteinaceous compounds.

While the device is primarily contemplated for use in human patients, the inventors also contemplate that the invention will have veterinary uses or product development purposes in equine, bovine, canine, feline, and other mammalian species.

Further, while the invention has been described in connection with the above described embodiments, it is not intended to limit the scope of the invention to the particular forms set forth, but on the contrary, it is intended to cover such alternatives, modifications, and equivalents as may be included within the scope of the invention. Still further, the scope of the present invention fully encompasses other embodiments that may become obvious to those skilled in the art and the scope of the present invention is limited only by the appended claims.

What is claimed is:

1. Apparatus for draining excess fluid from a patient's peritoneal cavity comprising:
   a hollow cylinder configured to be disposed across a wall of a patient's bladder, the hollow cylinder having an inflow end and an outflow end including a deformable flange configured to be deployed and anchored within the bladder;
   an implantable pump having an inlet port and an outlet port;
   a first elongated flexible tube coupled in fluid communication between the inflow end of the hollow cylinder and the outlet port of the implantable pump;
   a second elongated flexible tube having an exterior diameter, an outlet end coupled to the inlet port of the implantable pump, and an inlet end;
   a perforated receptacle coupled to the inlet end of the second elongated flexible tube, the perforated receptacle having a substantially greater diameter than the exterior diameter of the second elongated flexible tube and a multiplicity of pores configured to permit inflow of peritoneal fluid into the perforated receptacle while retarding ingrowth of tissue; and
   an electronic valve regulating flow of fluid between the outlet end of the implantable pump and the outflow end of the hollow cylinder,
   wherein the apparatus is configured to be triggered via an electric or radio signal.

2. The apparatus of claim 1, wherein the electronic valve is disposed within the hollow cylinder.

3. The apparatus of claim 1, wherein the deformable flange facilitates coupling of the hollow cylinder to the wall of the bladder.

4. The apparatus of claim 1, wherein the perforated receptacle comprises a mesh.

5. The apparatus of claim 1, wherein the electronic valve is controlled through a signal selected from the group of a pressure signal, a mechanical signal, a magnetic signal, an electric signal, and an electromagnetic frequency (EMF) signal.

6. The apparatus of claim 5, wherein the EMF signal is a radio signal.

7. The apparatus of claim 1, wherein the apparatus is configured to provide unidirectional flow of the fluid.

8. The apparatus of claim 1, wherein the apparatus is configured to prevent the spread of infection.

9. The apparatus of claim 8, wherein the apparatus is configured to prevent the spread of infection by providing one or more antibiotic dispensers.

10. The apparatus of claim 8, wherein the apparatus is configured to prevent the spread of infection by providing a material selected from the group consisting of a bacteriostatic material, a bacteriocidal material, an antibiotic eluting material, a material comprising entrained radioisotopes, a material comprising a heating element, a bioactive plastic, and a surface encouraging epithelialization.

11. The apparatus of claim 8, wherein the apparatus is configured to prevent the spread of infection by providing a coating that prevents bacterial adhesion.

12. The apparatus of claim 1, further comprising an anti-clogging device.

13. The apparatus of claim 12, wherein the anti-clogging device is selected from the group consisting of an active ultrasonic component, a sleeve disrupting the flow of the fluid upon active agitation, a surfaces encouraging epithelialization, an enzyme eluting material, a chemical eluting surface, an intermittent plunger mechanism, and a coating preventing adhesion of proteinaceous compounds.

* * * * *